United States Patent [19]

Wright, Jr.

[11] 4,016,883
[45] Apr. 12, 1977

[54] MEDICAL CLAMP FOR OCCLUDING INTRACRANIAL BLOOD VESSELS

[76] Inventor: Sanford J. Wright, Jr., 2000 Baltimore Road, Rockville, Md. 20850

[22] Filed: Nov. 11, 1975

[21] Appl. No.: 624,302

[52] U.S. Cl. .............................. 128/325; 128/346
[51] Int. Cl.² .................. A61B 17/12; A61B 17/08
[58] Field of Search ..................... 128/23, 325, 346

[56] References Cited

UNITED STATES PATENTS

| | | | |
|---|---|---|---|
| 2,796,867 | 6/1957 | Pearson | 128/346 |
| 3,541,591 | 11/1970 | Hoegerman | 128/346 X |
| 3,687,131 | 8/1972 | Rayport et al. | 128/346 X |
| 3,880,166 | 4/1975 | Fogarty | 128/325 |
| 3,911,926 | 10/1975 | Peters | 128/325 |

FOREIGN PATENTS OR APPLICATIONS 1,957,855  5/1971  Germany ........................ 128/325

*Primary Examiner*—Channing L. Pace
*Attorney, Agent, or Firm*—Charles M. Leedom

[57] ABSTRACT

This invention relates to a medical clamp for controllably occluding extremely small body vessels such as blood vessels within the intracranial or intraspinal areas of the human body. The disclosed clamp is preferably formed from a U-shaped unitary body of transparent, resilient elastomeric biologically inert material such as Tygon or Silastic wherein the leg members of the U-shaped body are controllably brought together to occlude a vessel placed therebetween by means of a flexible line or spring. Several embodiments are disclosed illustrating various expedients for securing the flexible line such as a sliding friction device or latch plate, and for operating and securing the string mechanism. All embodiments include means for measuring and detecting the termination of fluid flow through a vessel being occluded. Such measuring or detecting means permit the use of only that amount of pressure and no more than is necessary to cause vessel occlusion.

31 Claims, 8 Drawing Figures

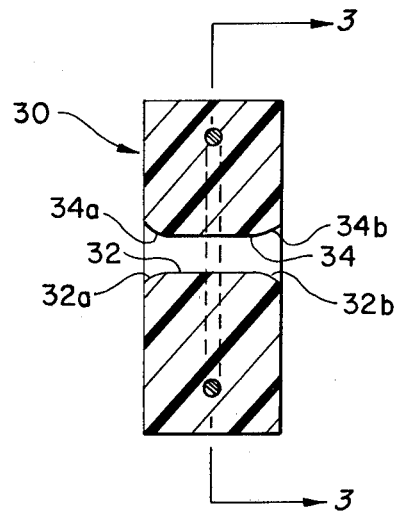
FIG. 4
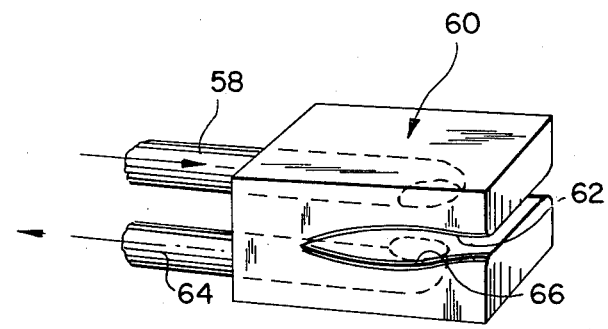
FIG. 5
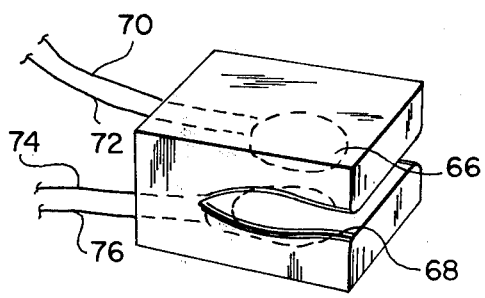
FIG. 6
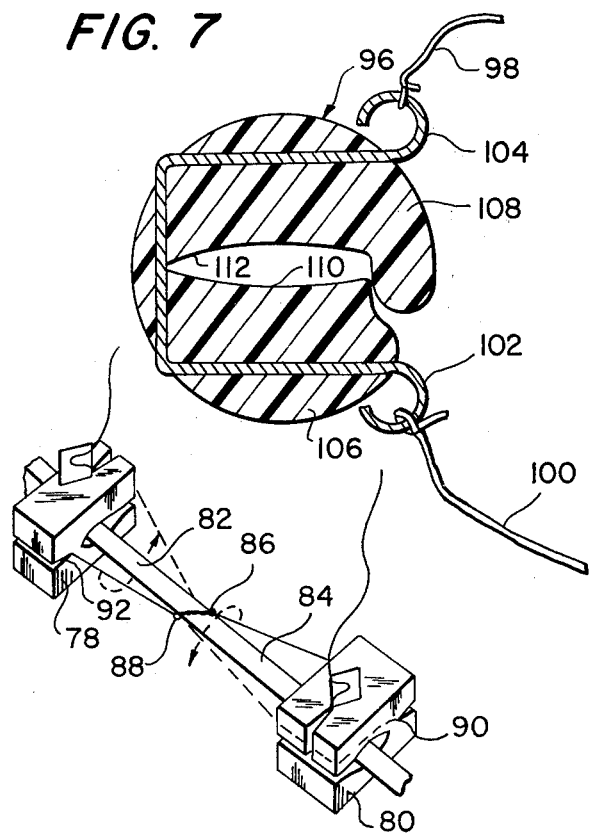
FIG. 7
FIG. 8

MEDICAL CLAMP FOR OCCLUDING INTRACRANIAL BLOOD VESSELS

BACKGROUND OF THE INVENTION

1. Field of the Invention

This invention relates to body vessel clamps particularly adapted for occluding blood vessels within the cranial or spinal cavity.

2. Discussion of the Prior Art

Temporary occlusion of body vessels to prevent the flow of fluid within a vessel during surgical operations has long been necessary. In 1960 Jacobson and Suarez published a fundamental work clearly establishing a successful technique for uniting vessels of only 1–2 mm in diameter. See Jacobson, J.H. and Suarez, E.I., "Microsurgery in Anastomosis of Small Vessels", Surgical Forum, Clinical Congress 1960 Vox XI, p. 243–253, Chicago: American College of Surgeons. A vast array of mechanical contrivances have since been developed particularly to facilitate the microvascular surgeon in accomplishing this result within the least possible time while simultaneously minimizing vessel trauma. Early in the development of the microvascular art, only relatively large excessively powerful metal spring clamps such as bulldog clamps were available. See Chase, M.D. and Schwartz, S.I., "A Technique of Small Artery Anastomosis," Surgical Gynecology and Obstetrics, Vol. 116, pages 381–84, 1963. In addition to being excessively large, these conventional clamps failed to adequately maintain a stable anastomotic position. In this regard, some experts in the field have suggested the use of traction stitches, Cobbett J. "Small Vessel Anastomosis", British Journal of Plastic Surgery, Vol. 20, pages 16–20, 1967 and O'Brien B Mc et al; "Microvascular Surgical Technique", Medical Journal of Australia vol. 1, pages 722–775, 1970. Microvascular occluding units employing a pair of vascular clips bonded together by means of a slender frame has proved useful in maintaining vessel ends in proximity to one another during the suturing process. See Henderson P.N., et al., "An Adjustable Double Microvascular Clamp", Medical Journal of Australia, Vol 1, pages 715–717 1970. In some instances the slender frame bonding two vascular clips to one another may have "cleats" for attaching preliminary anastomotic sutures and thereby stabilizing the site of union. See Acland, R., "A Device for Holding Stay Sutures and a New Vascular Clamp", Surgery, Vol. 75, pages 185–187, February 1974. While any or all of the above mentioned techniques may be of particular value for more exposed sites of microvascular union (see Lendray, P. "Anastomosis of Digital Vessels", Medical Journal of Australia, Vol. 2, pages 723–725, 1969) they frequently prove awkward in the cramped intracranial and intraspinal operative fields, Yasargil, M.G. and Donaghy, R.M.P., "Microvascular Surgery", C. V. Mosby Co., St Louis, 1967.

Within the patent literature the need for an atraumatic vessel occluder has been recognized as disclosed in U.S. Pat. No. 3,880,166 to Fogarty. The Fogarty patent discloses an instrument for occlusion of small blood vessels including a substantially rigid plastic pad having a throat at one end and a passageway at the other end for receiving a resilient tape which may be selectively positioned to entrap and occlude a blood vessel between the pad and one end of the tape. While useful in many situations, the Fogarty clamp does not readily permit control of increased clamping pressure to a level which is just sufficient to occlude the vessel yet insufficient to cause vessel trauma. Furthermore, the Fogarty clamp tends to pinch the occluded vessel in a localized area defined by the width of the flexible tape being used thereby increasing the possibility of injury to the vessel. Other types of vessel occluding clips are known which do not apply such localized pressure such as disclosed in U.S. Pat. Nos. 3,865,944 to Sandi; 3,856,016 to Davis and 3,840,018 to Heifetz but these clips all require clumsy application instruments which are difficult to maneuver within small body cavities and which impede the surgeon's ability to accurately control the clamping pressure.

Techniques for occluding other body vessels have been suggested for application to blood vessel. For example, Berman, H. et al ("Method of Intestinal Anastomosis Without the Use of Clamps," Annals of Surgery, April 1953, pages 548–550) discloses the use of a piece of foam wrapped about a body vessel and pulled tight by means of a surrounding suturing line. The difficulty of inserting, positioning and tying a piece of foam rubber around a very small blood vessel by means of a separate suturing line within an extremely small body cavity is self evident. In summary the prior art has failed to teach a body vessel clamp which satisfies the sometimes conflicting goals of operability in extremely small spaces plus minimization of vessel trauma.

SUMMARY OF THE INVENTION

It is the object of the subject invention to provide a medical clamp for controlled occlusion of a body vessel which overcomes the difficiencies of the prior art noted above. More particularly, a medical clamp is disclosed which is easily operated while permitting both extremely precise occlusion and stable maintainence of the anastomotic position. A particular advantage of the subject clamp is its small size and lack of encumbering attachments which make it especially advantageous in cramped intracranial locations wherein previously known clamps are unsuited.

A more particular object of the subject invention is the provision of a medical clamp for controlled occlusion of a body vessel including vessel engaging means for applying pressure to generally opposed sides of a body vessel, wherein the vessel engaging means includes a pair of members having first and second surfaces for engaging the vessel to be occluded. Also included are connecting means for connecting the members to permit movement between a first position in which the vessel engaging surfaces are spaced apart to receive a vessel and a second position in which the vessel engaging surfaces are spaced sufficiently close to occlude the vessel placed therebetween. To control the pressure applied by the vessel engaging surfaces, two alternate mechanical methods are employed: (1) a flexible line or wire/line combination and (2) an adjustable spring. When a flexible line is provided, one portion thereof is fixedly connected to the vessel engaging means and another portion of the line is secured by a securing means for selectively securing the second portion to the vessel engaging means to hold the members in a selected position intermediate the first and second positions. In the adjustable spring embodiment, a variable occluding pressure is obtained by varying the amount of pressure applied to the vessel engaging surfaces by the spring member.

Yet another object of the subject invention is the provision of a medical clamp embodying the structure defined above wherein the vessel engaging means and the connecting means form a unitary U-shaped body of elastomeric material.

Still another object of the subject invention is the provision of a medical clamp including the above described elements and further including vessel engaging surfaces formed on the inside opposed surfaces of the members referred to above wherein the surfaces have a generally concave configuration in cross section defined by a plane passing perpendicularly through the vessel engaging surfaces in a longitudinal direction extending from the base of the U-shaped body to the distal ends of the U-shaped legs. These vessel engaging surfaces are further characterized by rounded portions adjacent the lateral sides of the U-shaped body which rounded portions further protect the vessel around which the clamp is placed.

Still another object of the subject invention is the provision of a medical clamp having characteristics noted above and further including leg engaging surfaces on the inside of each leg member adjacent the distal ends thereof whereby the leg engaging surfaces are more closely spaced together than are the vessel engaging surfaces such that the leg engaging surfaces are brought into contact as the flexible line is subjected to tension or the adjustment lines release the spring energy thereby containing a vessel within the space between the vessel engaging surfaces.

Many more specific objects of the subject invention will become apparent by reference to the following description of the preferred embodiments and the drawings referred to therein.

BRIEF DESCRIPTION OF THE DRAWINGS

FIG. 4 is a cross-sectional view of the medical clamp illustrated in FIG. 3, taken along lines 4—4;

FIG. 5 is a perspective view of a medical clamp formed in accordance with an alternative embodiment of the subject invention employing fiber optics for remotely determining the point at which fluid ceases to flow through a vessel around which the clamp is placed; and FIG. 6 is a perspective view of yet another embodiment of a medical clamp formed in accordance with the subject invention including electrical transducers for measuring the flow of fluid through a body vessel around which the clamp is placed;

FIG. 7 is a cross-sectional view of a medical clamp formed in accordance with the subject invention including a spring for selectively applying pressure to the vessel engaging surfaces; and FIG. 8 is a perspective view of a pair of clamps formed in accordance with the subject invention deployed in an anastomotic operation.

DETAILED DESCRIPTION OF THE PREFERRED EMBODIMENTS

Figure 1:
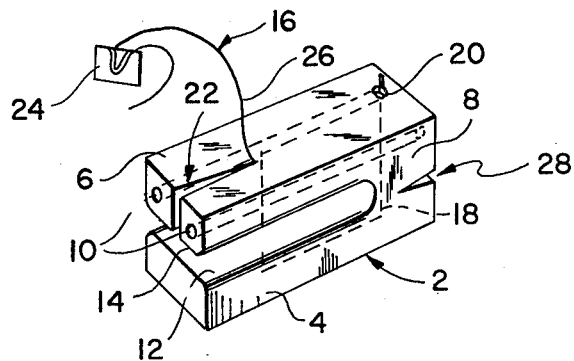
FIG. 1 is a perspective view of a medical clamp designed in accordance with the subject invention formed from a U-shaped unitary body of elastomeric material.

Referring to FIG. 1 a medical clamp is disclosed having particular application within extremely small body cavities such as intracranial areas wherein occlusion and anastomosis of extremely small blood vessels (2mm and less) are often required. The disclosed clamp is formed from a U-shaped unitary body 2 of elastomeric material which is preferably transparent to permit greater visibility as will be explained in more detail below. One type of material which has been found to be particularly desirable is a transparent, resilient synthetic rubber-like material known by the trademark TYGON of the U.S. Stoneware Co. or inert material known by the trademark SILASTIC of Dow Corning. These materials evidence the desired degree of flexibility while at the same time retaining a generally U-shaped configuration to permit the clamp to be readily inserted about a blood vessel when the clamp is in a first unstressed condition.

The clamp of FIG. 1 is characterized by first and second members 4 and 6 which constitute respectively the legs of the U-shaped body 2. The leg members 4 and 6 are interconnected by a base portion 8 of the body 2. Although not necessary, member 6 may be made stiffer than member 4 by inserting 00 stainless steel stiffening rods 10 to restrict the primary flexing within the unitary body to the base portion 8 and the leg member 4. The inside opposed surfaces 12 and 14 of leg members 4 and 6, respectively, are shaped to form first and second vessel engaging surfaces, respectively. As can be readily appreciated, members 4 and 6 constitute vessel engaging means for applying pressure to generally opposed sides of the body vessel.

The base portion 8 of the unitary body constitutes a connecting means for connecting members 4 and 6 to permit the movement of the members between a first position, illustrated in FIG. 1, in which the vessel engaging surfaces 12 and 14 are spaced apart to receive a vessel and a second position in which the vessel engaging surfaces are spaced sufficiently close to occlude a vessel placed therebetween. In order to control the pressure applied to the vessel, pressure controlling means are provided for controlling movement of the vessel engaging surfaces between the first and second positions and for holding the vessel engaging surfaces in any selected position intermediate the first and second positions. As illustrated in FIG. 1 the pressure controlling means includes a flexible line 16 having one portion fixedly connected to the unitary body 2. The flexible line may be formed from 6-0, 7-0 Nylon or Teflon suture material. As further illustrated in FIG. 1, portion 18 of the flexible line is knotted at 20 and extends through the base portion 8 along the exterior surface of leg member 6 back through a distal portion of leg member 6 into the space between the leg members. Leg member 4 is formed with an occluder groove 22 for frictionally receiving the flexible line after the clamp has been placed over a vessel to be occluded. Once the flexible line is properly positioned within occluder groove 22, a line stop means 24 slidably connected with a more distal portion of the flexible line is advanced into contact with leg member 6. The flexible line may be further drawn through the line stop means 24 to gradually and controllably close the interior passage of a body vessel placed between the vessel engaging surfaces. The line stop means 24 may be formed from any biologically inert synthetic polymer such as an approximately 1 × 1 × 2.5 mm piece of blue coronary occluding material through which passes portion 26 of the flexible line 16. Coronary occluding material is well known in the surgical arts and has flexible properties which make it ideal in the subject environment. In particular, a mass of coronary occluding material may be brought about the flexible line in such a manner that the flexible line can be pulled through the mass if sufficient force is applied. However, the coronary occluding material retains sufficient adhesive characteristics that when the pulling force is stopped, the mass tends to remain in a fixed position along the flexible line.

For reasons that will be apparent hereinafter, a traction groove 28 is formed in the base portion 8 of the unitary body 2 for receiving and retaining a suture line.

Although the operation of the disclosed medical clamp in FIG. 1 should be obvious from the above description, a summary of the operation follows in order to emphasize the advantages of the disclosed structure. The medical clamp of FIG. 1 is initially placed around a vessel when flexible line 16 is located outside of occluder groove 22. Once the clamp is in place around the vessel, the flexible line 16 is placed within occluder groove 22 and the line stop means 24 is advanced against the exterior surface of member 6. Since the unitary body 2 is preferably formed of transparent material, continued advancement of the stop means 24 may be ceased as soon as the vessel just blanches indicating that flow has been shut off. Heretofore the amount of pressure necessary for occluding a body vessel, particularly blood vessels, has not been easily determinable since the occluding clamp, to say nothing of the clamp application instruments, have tended to obscure the surgeon's vision of the vessel's condition.

Figure 2:
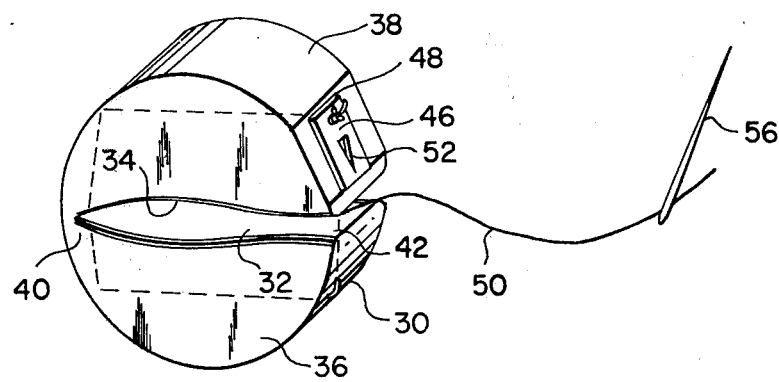
FIG. 2 is a perspective view of a medical clamp designed in accordance with an alternative embodiment of the subject invention formed from a U-shaped unitary body of elastomeric material having a generally cylindrical outer surface.
Figure 3:
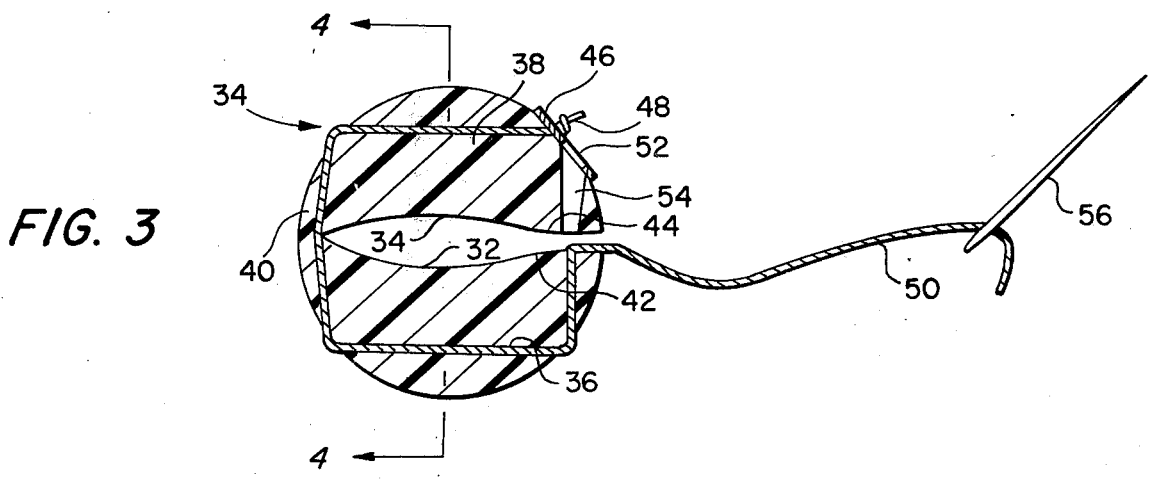
FIG. 3 is a cross-sectional view of the medical clamp illustrated in FIGS. 2 and 4 taken along lines 3—3 of FIG. 4.

Another embodiment of the invention is illustrated in FIGS. 2–4 wherein a medical clamp 30 is disclosed including a U-shaped unitary body having a generally cylindrical outer surface. The clamp of FIGS. 2–4 is further characterized by a pair of vessel engaging surfaces 32 and 34 formed on the interior opposed surfaces of leg members 36 and 38, respectively. FIG. 3 is a cross-section of the clamp illustrated in FIG. 2 taken along a plane (illustrated by lines 3—3 in FIG. 4) passing perpendicularly through the vessel engaging surfaces 32 and 34 in a longitudinal direction extending from the base 40 of U-shape body 30 to the distal ends of the leg members 36 and 38. As is illustrated quite clearly in FIG. 3, the vessel engaging surfaces 32 and 34 have a generally concave configuration.

As is further illustrated in FIG. 3, legs 36 and 38 include leg engaging surfaces 42 and 44 adjacent the distal ends of the legs. The leg engaging surfaces 42 and 44 are more closely spaced than are the vessel engaging surfaces when the clamp is in a first unstressed condition. Accordingly, the leg engaging surfaces 42 and 44 engage one another before the vessel engaging surfaces 32 and 34 reach the second vessel occluding position to thereby insure retention of a vessel between the vessel engaging surfaces.

The clamp of FIGS. 2–4 further includes a latch plate 46 having a first aperture for receiving the knotted end of a flexible line 50 which then extends through leg member 38, base portion 40, leg member 36 and emerges through leg engaging surface 42. A second aperture 52 in the form of a triangular slot is positioned over a passage 54 formed in leg member 38. Passage 54 extends toward and emerges through leg engaging surface 44 at a position directly opposite the position at which flexible line 50 emerges from leg engaging surface 42.

The operation of medical clamp of FIG. 2 is now apparent. Once the clamp is inserted over a body vessel, flexible line is passed through passage 54 and aperture 52. As the flexible line is drawn tight, leg engaging surfaces 42 and 44 come into contact so as to entrap the body vessel between surfaces 32 and 34. Further tightening of the flexible line causes vessel engaging surfaces 32 and 34 to push in upon the vessel thereby causing occlusion.

As illustrated in FIGS. 2 and 3, flexible line 50 terminates in a needle 56 which is adapted to be inserted through passage 54 and aperture 52 as soon as the clamp is placed over a body vessel to be occluded. By drawing the flexible line tightly until the vessel around which the clamp is placed "blanches" and then moving the flexible line forwardly in the triangular aperture 52, the clamp may be held in a vessel occluding position.

FIG. 4 illustrates the configuration of the edge portions of the vessel engaging surfaces 32 and 34. More particularly, vessel engaging surface 34 is illustrated as having rounded portions 34a and 34b at each edge adjacent the side of the clamp. Similarly, vessel engaging surface 32 includes rounded edge portions 32a and 32b adjacent the sides of the medical clamp. By providing rounded edge portions on the vessel engaging surfaces, the chance of causing trauma to an occluded vessel is further decreased.

Turning now to FIG. 5, a medical clamp is illustrated of the type generally disclosed in FIG. 1 wherein some of the details such as the occluding groove and traction groove have been omitted merely for clarity purposes. As is apparent, the clamp of FIG. 5 differs from previously disclosed embodiments by the provision of a first fiber optic 58 which enters the base portion of the unitary body 60 and extends inwardly to a point adjacent the vessel engaging surface 62 such that light passing into a remote end of the first fiber optic 58 will be transmitted into the unitary body and be projected through the vessel engaging surface into a body vessel placed within the clamp. A second fiber optic 64 is provided and extends through the base portion of the unitary body into a position adjacent vessel engaging surface 66 at a point directly opposite the point of vessel engaging surface 62 through which light from fiber optic 58 emerges. In this manner, fiber optic 64 is adapted to receive light transmitted through a body vessel around which the clamp has been placed. By providing a photosensitive element (not illustrated), at a remote end of fiber optic 64, the amount of light transmitted through a vessel during the process of closing the clamp of FIG. 5 can be monitored so as to permit the application of only that amount of occluding pressure which is necessary to stop the flow of fluid within a body vessel around which the clamp has been placed.

FIG. 6 illustrates yet another embodiment of the subject invention wherein a medical clamp is illustrated of the general design illustrated in FIG. 1 but wherein some of the details have been omitted so as to emphasize the differences in the disclosed embodiment. More particularly, FIG. 6 illustrates the provision of electrical sensing transducers 66 and 68 connected by four leads 70 through 76 to electrical circuitry (not illustrated). The electrical sensing transducers 66 and 68 may be any conventional type of electrical devices which are adapted to sense the condition and more particularly the flow through a body vessel so as to accurately determine the effect with clamping pressure is having upon a vessel around which the clamp has been placed. Transducers 66 and 68 may therefore take the form of capacitor plates wherein changes in the flow rate effect the dielectric between the plates. Alternatively, elements 66 and 68 may be electrical coils for transmitting and receiving, respectively, a magnetic field modified by the flow of body fluid through the vessel being clamped. Still another possibility would be merely to form elements 66 and 68 as contacts for measuring the resistivity of the body vessel.

Alternately, the encircling flexible line of the above described embodiment may be replaced by a thin U-shaped spring element 94 embedded in the unitary body 96 as illustrated in FIG. 7. A pair of adjustment lines 98 and 100 are connected to opposite ends 102 and 104 respectively, of the U-shaped spring element 94 which protrude outside of the unitary body 96. The adjustment lines are employed to pull open the occluding leg member 106 and 108 to show a vessel to be fitted into the space between vessel engaging surfaces 110 and 112. The tension on the adjustment lines is then slowly released and the end point of occlusion noted. If excessive spring energy is present, the occluding leg member may be opened somewhat widely a second time to stretch the spring beyond its spring return point to reduce the closing energy somewhat. In this way the exact spring energy required to reach an occluding end point is achieved.

The medical clamp has been disclosed which has particular utility in the occlusion of extremely small body vessels such as blood vessels within the intracranial areas. Because of the extreme simplicity of design, the disclosed clamp may be extremely small. For example, the clamp illustrated in FIG. 2 may have an outside diameter ranging from 3 mm down to as small as 1 mm with a total width that is the distance from one planar side to the other planar side ranging from 2 mm down to as small as 0.5 mm. In the unstressed condition, the vessel engaging surfaces of a medical clamp such as illustrated in FIG. 2 are separated by a distance of from 0.3 mm down to as little as 0.1 mm. Since the disclosed medical clamp does not require specialized application instruments, use during an operation is greatly simplified over medical clamps known heretofore.

The disclosed clamp design has particular utility in surgical procedures involving a blood vessel anastomosis wherein the resected ends of two blood vessels are joined together such as illustrated in FIG. 8. To prevent fluid flow and to maintain a stable anastomosis, a pair of medical clamps 78 and 80 as illustrated in FIG. 1 are deployed near the resected end of the blood vessels 82 and 84, respectively.

In blood vessel anastomosis a pair of traction stitches 86 and 88 may be placed on opposite sides of the joint between the pair of blood vessels 82 and 84. As illustrated stitches 86 and 88 are formed from suturing line having one end of sufficient length to extend toward one of the clamps 78 and 80 where the suturing line is frictionally held in the traction grooves 90 and 92, respectively, of the clamps. When the front wall of the anastomosis has been completed, the suturing line is removed from the traction grooves and wrapped in opposite direction around each clamp as illustrated in dotted lines with one suturing line being first passed beneath the anastomosis. By this procedure the back side of the vessel joint is exposed for completion of the anastomotic operation. On some occasions the pair of clamps may simply be rotated as an assembly to expose the back side of the vessel joint. In still another variation of the above described technique, the traction grooves may be eliminated altogether by merely passing a needle through the body of material making up the medical clamp.

A distinct advantage of the disclosed clamp design is its ability to be slowly released in order to permit limited fluid flow through an anastomosis for testing purposes. If the anastomosis is not fluid tight, the clamp may be immediately reclosed in order that additional work can be performed on the joint.

Ease of operation, gentle precise occlusion, stable maintenance of anastomotic position and small size without encumbering attachments make the disclosed medical clamp particularly advantageous in intracranial and intraspinal locations.

I claim:

1. A medical clamp for controlled occlusion of a body vessel, comprising
   a. vessel engaging means for applying pressure to generally opposed sides of a body vessel, said vessel engaging means including a pair of members having first and second vessel engaging surfaces, respectively;
   b. connecting means for connecting said members to permit movement of said members between a first position in which said vessel engaging surfaces are spaced apart to receive a vessel and a second position in which said vessel engaging surfaces are spaced sufficiently close to occlude a vessel placed therebetween;
   c. pressure controlling means connected with said vessel engaging means for controlling the pressure applied to a vessel by controlling movement of said vessel engaging surfaces between said first and second positions and for holding said vessel engaging surfaces in any selected position intermediate said first and second positions, said pressure controlling means including
      1. a flexible line having one portion thereof fixedly connected to said vessel engaging means, and
      2. line securing means for selectively securing another portion of said flexible line to said vessel engaging means to hold said members in the selected intermediate position.

2. A medical clamp as defined in claim 1, wherein said one portion of said flexible line is connected with one said member and said line securing means is connected with the other said member.

3. A medical clamp as defined in claim 2, wherein said vessel engaging means and said connecting means are formed from a unitary U-shaped body of elastomeric material wherein said members form the respective legs of the U-shaped body and said connecting means forms the base of the U-shaped body.

4. A medical clamp as defined in claim 3 wherein said body is formed of transparent material.

5. A medical clamp as defined in claim 4 wherein said transparent material is selected from the group consisting of Tygon and Silastic.

6. A medical clamp as defined in claim 1, wherein said members are formed of bendable resilient material.

7. A medical clamp as defined in claim 4, wherein one member is stiffer than the other said member.

8. A medical clamp as defined in claim 7, wherein said one member includes at least one metal stiffening rod.

9. A medical clamp as defined in claim 1, wherein said line securing means further includes a portion of the other said member containing a groove shaped to receive a portion of the flexible line after a vessel has been placed between said vessel engaging surfaces.

10. A medical clamp as defined in claim 9, wherein said pressure controlling means includes a line stop means slidably connected with said flexible line for engaging and holding said flexible line at any selected position therealong, whereby the stop means may be advanced along the flexible line into contact with said other member after said flexible line has been inserted into said groove whereupon continued advance of said stop means will draw said vessel engaging surfaces more closely together to gradually and controllably close the interior passage of a body vessel placed between the vessel engaging surfaces.

11. A medical clamp as defined in claim 9, wherein the proximal end of the flexible line is secured to said first member by placing said flexible line in a groove formed in the outer surface of said one member and through a passage in said connecting means terminating in a knot tied in said flexible line.

12. A medical clamp as defined in claim 1, wherein said connecting means further contains a traction groove for receiving one portion of a suture line adapted to be connected with a vessel anastomosis.

13. A medical clamp as defined in claim 3, wherein said vessel engaging surfaces are formed by the inside opposed surfaces of said members, said surfaces having a generally concave configuration in cross-section defined by a plane passing perpendicularly through said vessel engaging surfaces in a longitudinal direction extending from the base of said U-shaped body to the distal ends of said U-shaped body legs.

14. A medical clamp as defined in claim 13, wherein said vessel engaging surfaces include rounded portions adjacent the lateral sides of said U-shaped body.

15. A medical clamp as defined in claim 1, wherein said legs of said U-shaped body include leg engaging surfaces adjacent the distal ends of said legs, said leg engaging surfaces being more closely spaced than said vessel engaging surfaces when said vessel engaging surfaces are in said first position, whereby said leg engaging surfaces are adapted to engage one another before said vessel engaging surfaces reach said second position to thereby insure retention of a vessel placed between said vessel engaging surfaces.

16. A medical clamp as defined in claim 3 wherein the exterior shape of said U-shaped body is generally cylindrical.

17. A medical clamp as defined in claim 1, wherein said flexible line includes a needle at the distal end thereof and said securing means includes a latch plate containing a narrowing slot large enough at one end to permit easy passage of said needle and flexible line therethrough and gradually narrowing toward the opposite end to permit the flexible line to be frictionally engaged along said other portion of said flexible line.

18. A medical clamp as defined in claim 3, wherein said flexible line completely encircles said vessel engaging surfaces when said other portion is secured by said securing means.

19. A medical clamp as defined in claim 18, wherein a proximal portion of said flexible line is embedded in said unitary U-shaped body including said legs and said base.

20. A medical clamp as defined in claim 15, wherein said flexible line completely encircles said vessel engaging surfaces when said other portion is secured by said securing means, further wherein said flexible line emerges from said unitary body from said leg engaging surface of said one member and said another member includes a passage for receiving a portion of said flexible line leading to said securing means.

21. A medical clamp as defined in claim 3, wherein said U-shaped body includes exterior surfaces which form an exterior circular cross-section defined by a cross-sectional plane passing through said body perpendicularly to said vessel engaging surfaces in a longitudinal direction extending from the base of said body to the distal ends of said legs.

22. A medical clamp as defined in claim 21, wherein said exterior circular cross-section has a diameter greater than 1 mm and less than 3 mm, said vessel engaging surfaces being separated by a distance greater than 0.1 mm and less than 0.3 mm, and said exterior lateral width of said unitary body measured in a perpendicular direction to said cross sectional plane being less than 0.5 mm and more than 2.0 mm.

23. A medical clamp as defined in claim 1, further including means for remotely sensing the condition of the vessel to be occluded.

24. A medical clamp as defined in claim 23, wherein said sensing means includes fiber optics partially embedded within said members so as to project light toward and receive light from a body vessel around which the clamp is placed.

25. A medical clamp as defined in claim 23, wherein said sensing means includes electrical sensors for sensing the flow of body fluids to a vessel around which the clamp is placed.

26. A medical clamp for controlled occlusion of a body vessel, comprising
 a. vessel engaging and sensing means for applying pressure to generally opposed sides of a body vessel and for determining when sufficient pressure has been applied to occlude a vessel, said vessel engaging means including first and second vessel engaging surfaces;
 b. connecting means for connecting said first and second vessel engaging surfaces to provide for movement of said members between a first position in which said vessel engaging surfaces are spaced apart to receive a vessel and a second position in which said vessel engaging surfaces are spaced sufficiently close to occlude a vessel placed therebetween; and
 c. pressure controlling means connected with said vessel engaging means for controlling the pressure applied to a vessel by controlling movement of said vessel engaging surfaces between said first and second positions and for holding said vessel engaging surfaces in any selected position intermediate said first and second positions.

27. A medical clamp as defined in claim 26, wherein at least one portion of said vessel engaging and sensing means is formed of transparent material through which the portion of a vessel placed between said first and second vessel engaging surfaces may be viewed.

28. A medical clamp as defined in claim 26, wherein said vessel engaging and sensing means and said connecting means is formed by a unitary body of transparent material through which the portion of a vessel placed between said first and second vessel engaging surfaces may be viewed.

29. A medical clamp as defined in claim 26, wherein said vessel engaging and sensing means includes optic fibers for optically projecting light toward and receiving light from the portion of a vessel placed between said first and second vessel engaging surfaces.

30. A medical clamp as defined in claim 26, wherein said pressure controlling means includes a U-shaped spring element and means connected with the ends of said U-shaped spring element to adjustably control the pressure applied by said spring element to said vessel engaging surfaces.

31. A medical clamp as defined in claim 26, wherein said pressure controlling means includes a flexible line connected with said vessel engaging means.

* * * * *